US009291624B2

(12) United States Patent
Ankenbauer et al.

(10) Patent No.: US 9,291,624 B2
(45) Date of Patent: Mar. 22, 2016

(54) VACCINE DIAGNOSTICS

(75) Inventors: Robert G. Ankenbauer, Kalamazoo, MI (US); Lynn D. Nelson, Kalamazoo, MI (US); Nancee L. Oien, Kalamazoo, MI (US); Siao-Kun W. Welch, Kalamazoo, MI (US)

(73) Assignee: Zoetis Services LLC, Florham Park, NJ (US)

( * ) Notice: Subject to any disclaimer, the term of this patent is extended or adjusted under 35 U.S.C. 154(b) by 21 days.

(21) Appl. No.: 14/239,917

(22) PCT Filed: Aug. 10, 2012

(86) PCT No.: PCT/IB2012/054092
§ 371 (c)(1),
(2), (4) Date: May 6, 2014

(87) PCT Pub. No.: WO2013/027149
PCT Pub. Date: Feb. 28, 2013

(65) Prior Publication Data

US 2014/0302488 A1 Oct. 9, 2014

Related U.S. Application Data

(60) Provisional application No. 61/526,792, filed on Aug. 24, 2011.

(51) Int. Cl.
*G01N 33/569* (2006.01)
*C12Q 1/70* (2006.01)

(52) U.S. Cl.
CPC .... *G01N 33/56983* (2013.01); *G01N 2333/183* (2013.01); *G01N 2469/20* (2013.01)

(58) Field of Classification Search
None
See application file for complete search history.

(56) References Cited

U.S. PATENT DOCUMENTS

| | | | | |
|---|---|---|---|---|
| 6,001,613 | A | 12/1999 | Donis et al. | |
| 6,174,667 | B1 | 1/2001 | Huchzermeier et al. | |
| 6,455,264 | B1 | 9/2002 | Baumeister et al. | |
| 2014/0302488 | A1* | 10/2014 | Ankenbauer et al. | 435/5 |

FOREIGN PATENT DOCUMENTS

| | | | |
|---|---|---|---|
| WO | WO 2010/064164 | * | 6/2010 |
| WO | 2013/027149 A1 | | 2/2013 |

OTHER PUBLICATIONS

Vilcek et al. (Virus Research. 2005; 108: 187-193).*
Kashmiri et al. (Methods. 2005; 36:25-34).*
Tamura et al. (Journal of Immunology. 2000; 164:1432-1441).*
Greenspan et al (Nature Biotechnology. 17; 10:936-937 (1999).*
Yugang et al. "Construction of chimeric bovine viral diarrhea viruses containing glycoprotein Erns of heterologous pestiviruses and evaluation of the chimeras as potential marker vaccines against BVDV" Vaccine vol. 30 pp. 3843-3848 (2012).
Beer et al., "Novel Marker Vaccines Against Classical Swine Fever", Vaccine, vol. 25 pp. 2665-5670 (2007).
Dong et al., "Marker Vaccine Strategies and Candidate CSFV Marker Vaccines", Vaccine, 25(2):205-230 (2007).
Grego et al., "Development and Application of an Enzyme-linked Immunosorbent Assay for Detection of Bovine Viral Diarrhea Antibody Based on Erns Glycoprotein Expressed in a Baculovirus System", J. Vet. Diagn. Invest., 19(1):21-27 (2007).
Gripshover et al., "Variation in Erns Viral Glycoprotein Associated with Failure of Immunohistochemistry and Commercial Antigen Capture ELISA to Detect a Field Strain of Bovine Viral Diarrhea Virus", Veterinary Microbiology 125:11-21 (2007).
Ronecker et al., "Formation of Bovine Viral Diarrhea Virus E1-E2 Hetrodimers in Essential for Virus Entry and Depends on Charged Residues in the Transmembrane Domains", J. Gen Virol., 89(9):2114-2121 (2008).
De Smit et al., "Chimeric (Marker) C-strain Viruses Induce Clinical Protection Against Virulent Classical Swine Fever Virus (CSFV) and Reduce Transmission of CSFV Between Vaccinated Pigs", Vaccine, 19(11-12):1467-1476 (2001).
Van Gennip et al., "Chimeric Classical Swine Fever Viruses Containing Envelope Protein Erns or E2 of Bovine Viral Diarrhoea Virus Protect Pigs Against Challenge with CSFV and Induce a Distinguishable Antibody Response", Vaccine, 19(4-5)447-459 (2001).
Ruben O. Donis, et al., Neutralizing Monoclonal Antibodies to Bovine Viral Diarrhea Virus Bind to the 56K to 58K Glycoprotein, J. gen. Virol. (1988), 69, 77-86.
Wayne V. Coapi, DVM, PhD, et al., Characterization of panel of monoclonal antibodies and their use in the study of the antigenic diversity of bovine viral diarhhea virus, Am J Vet Res, vol. 51, No. 9, Sep. 1990, pp. 1388-1394.
Ellie M. Gripshover, et al., Variation of Erns viral glycoprotein associated with failure of immunohistochemistry and commercial antigen capture ELISA to detect a field strain of bovine viral diarrhea virus, Veterinary Microbiology 125 (2007) 11-21.
Yugang Luo, et al., Construction of chimeric bovine viral diarrhea viruses containing glycoprotein Erns of heterologous pestiviruses and evaluation of the chimeras as potential marker vaccines against BVDV, Vaccine 30 (2012) 3843-3848.

* cited by examiner

*Primary Examiner* — Shanon A Foley
(74) *Attorney, Agent, or Firm* — Gloria K. Szakiel

(57) ABSTRACT

The present invention relates to improved diagnostic methods and kits for differentiating between (a) animals administered a chimeric pestivirus, and (b) animals infected with a wild-type bovine viral diarrhea virus (BVDV) or immunized with a conventional BVDV vaccine.

12 Claims, No Drawings

VACCINE DIAGNOSTICS

CROSS-REFERENCE TO RELATED APPLICATIONS

This application is a national phase entry of international application number PCT/IB2012/054092, filed Aug. 10, 2012 which claims priority to U.S. Provisional Application No. 61/526,792, filed Aug. 24, 2011. The disclosure of the above-identified provisional application and the above-identified international application are herein incorporated by reference in their entireties.

FIELD OF THE INVENTION

The present invention relates to improved diagnostic methods and kits for differentiating between (a) animals administered a chimeric pestivirus, and (b) animals infected with a wild-type bovine viral diarrhea virus (BVDV) or immunized with a conventional BVDV vaccine.

BACKGROUND OF THE INVENTION

Pestiviruses, including bovine viral diarrhea virus (BVD virus, or BVDV), have been isolated from several species of animals, both domestic and wild. Identified hosts for BVDV include buffalo, antelope, reindeer and various deer species, while unique pestivirus species have been identified in giraffes and pronghorn antelope. BVDV is a small RNA virus of the family Flaviviridae. It is closely related to other pestiviruses which are the causative agents of border disease in sheep and classical swine fever in pigs.

Disease caused by BVDV particularly in cattle is widespread, and can be economically devastating. BVDV infection in cattle can result in breeding problems, and can cause abortions or premature births. BVDV is capable of crossing the placenta of pregnant cattle, and may result in the birth of persistently infected (PI) calves that are immunotolerant to the virus and persistently viremic for the rest of their lives. Infected cattle can also exhibit "mucosal disease", characterized by elevated temperature, diarrhea, coughing and ulcerations of the alimentary mucosa. These persistently infected animals provide a source for dissemination of virus within a herd and for further outbreaks of mucosal disease, and are highly predisposed to infection with microorganisms responsible for causing enteric diseases or pneumonia.

Among the BVDV vaccines currently available are those which contain chemically-inactivated wild-type virus, or those which contain modified-live (ML) BVDV. BVDV can be attenuated by repeated passage in bovine or porcine cells, or by chemically-induced mutations that confer a temperature-sensitive phenotype on the virus. However, existing inactivated and ML vaccines do not allow for the differentiation between vaccinated and naturally-infected animals.

A "marked" vaccine that could either contain an additional antigenic determinant which is not present in wild-type virus, or lack an antigenic determinant which is present in wild-type virus could be an effective tool for controlling BVDV infection in the field. US Patent Application 2010/0360055 (Luo et al., herein incorporated by reference in its entirety) describes the latter, a vaccine based upon a chimeric pestivirus vaccine in which the $E^{rns}$ protein of the BVDV is replaced with the $E^{rns}$ protein from a pronghorn pestivirus. This chimeric pestivirus was deposited as UC 25548 with ATCC®, and given the ATCC® deposit designation of PTA-9939. Accompanied by an appropriate diagnostic assay, use of this chimeric pestivirus would allow for the differentiation between animals to which it was administered, versus animals infected with wild-type BVDV or immunized with a conventional BVDV vaccine.

SUMMARY OF THE INVENTION

In one embodiment, a method is provided for determining whether an animal was exposed to a BVDV or immunized with a conventional BVDV vaccine, wherein the animal infected with BVDV or immunized with a conventional BVDV vaccine possesses an antibody that specifically binds to at least one $E^{rns}$ epitope which is present in BVDV, but which is not present in a chimeric pestivirus that no longer expresses an $E^{rns}$ protein from a BVDV, but expresses an $E^{rns}$ protein from a pronghorn pestivirus in a BVDV.

In one embodiment, a method is provided for determining the presence or absence of an antibody that specifically binds to a BVDV $E^{rns}$ protein, said method comprising the steps of:

a) obtaining a serum sample from the animal;
b) incubating said sample with pronghorn pestivirus $E^{rns}$ protein or a fragment thereof;
c) detecting in said sample the presence or absence of said antibody.

In another embodiment, a diagnostic kit is provided for determining whether an animal was exposed to a BVDV or immunized with a conventional BVDV vaccine, said kit comprising reagents capable of detecting antibodies to at least one $E^{rns}$ epitope that is present in BVDV, but which is not present in a chimeric pestivirus that no longer expresses an $E^{rns}$ protein from a BVDV, but expresses an $E^{rns}$ protein from a pronghorn pestivirus in a BVDV.

In a further embodiment, a use is provided for an antibody which binds to an epitope present in BVDV or a conventional BVDV vaccine, but which epitope is not present in a chimeric pestivirus that no longer expresses an $E^{rns}$ protein from a BVDV, but expresses an $E^{rns}$ protein from a pronghorn pestivirus in a BVDV.

In another embodiment, a method is provided for determining whether an animal possesses an antibody that specifically binds to a BVDV $E^{rns}$ protein, said method comprising the steps of:

a) obtaining a serum sample from the animal;
b) incubating said sample with pronghorn pestivirus $E^{rns}$ protein or a fragment thereof;
c) detecting in said sample the presence or absence of said antibody.

In another embodiment, a method is provided for determining the presence or absence of an antibody that specifically binds to a BVDV $E^{rns}$ protein, wherein the step of incubating said sample with pronghorn pestivirus $E^{rns}$ protein or a fragment thereof occurs prior to the step of detecting in said sample the presence or absence of said antibody.

In another embodiment, a method is provided for determining the presence or absence of an antibody that specifically binds to a BVDV $E^{rns}$ protein, wherein the step of incubating said sample with pronghorn pestivirus $E^{rns}$ protein or a fragment thereof occurs simultaneously with the step of detecting in said sample the presence or absence of said antibody.

In another embodiment, a method is provided for determining the presence or absence of an antibody that specifically binds to a BVDV $E^{rns}$ protein, wherein said antibody specifically binds to at least one epitope present in a BVDV $E^{rns}$ protein but not present in a pronghorn pestivirus $E^{rns}$ protein.

In another embodiment, a method is provided for determining the presence or absence of an antibody that specifically binds to a BVDV $E^{rns}$ protein, wherein the presence of said antibody indicates that the animal has either been infected with BVDV or immunized with a conventional BVDV vaccine.

In another embodiment, a method is provided for determining the presence or absence of an antibody that specifically binds to a BVDV $E^{rns}$ protein, wherein the absence of said antibody indicates that: a) the animal has not been 1) infected with BVDV, or 2) immunized with a conventional BVDV vaccine; or b) has been immunized with a chimeric pestivirus expressing a pronghorn pestivirus $E^{rns}$ protein.

In another embodiment, a method is provided for determining in a sample the presence or absence of an antibody that specifically binds to a BVDV $E^{rns}$ protein, wherein a serum sample is obtained from an animal that is susceptible to BVDV infections.

In another embodiment, a method is provided for determining in a sample the presence or absence of an antibody that specifically binds to a BVDV $E^{rns}$ protein, wherein a serum sample is obtained from an animal that is a bovine, ovine, caprine, or porcine species.

In another embodiment, a method is provided for determining in a sample the presence or absence of an antibody that specifically binds to a BVDV $E^{rns}$ protein, wherein a serum sample is obtained from an animal that is a bovine.

In another embodiment, a diagnostic kit is provided for determining the presence or absence of an antibody that specifically binds to a BVDV $E^{rns}$ protein, wherein said kit comprises reagents that facilitate the detection of the presence or absence of an antibody to at least one BVDV $E^{rns}$ epitope not present in a pronghorn pestivirus $E^{rns}$ protein, wherein one of said reagents is pronghorn pestivirus $E^{rns}$ protein or a fragment thereof.

In another embodiment, a diagnostic kit is provided for determining the presence or absence of an antibody that specifically binds to a BVDV $E^{rns}$ protein, wherein said kit comprises reagents that facilitate the detection of the presence or absence of an antibody to at least one BVDV $E^{rns}$ epitope not present in a pronghorn pestivirus $E^{rns}$ protein, wherein one of said reagents is an antibody that specifically binds to an epitope present in BVDV or a conventional BVDV vaccine, but which epitope is not present in a pronghorn pestivirus $E^{rns}$ protein.

In another embodiment, a diagnostic kit is provided for determining the presence or absence of an antibody that specifically binds to a BVDV $E^{rns}$ protein, wherein said kit comprises reagents for carrying out an assay selected from the group consisting of: an enzyme-linked immunosorbent assay (ELISA), a lateral flow assay, Western blotting, PCR, radioimmunoassay, solid phase radioimmunoassay, electrochemiluminescent assay, immunoblotting, immunoprecipitation, and immunostaining.

In another embodiment, the present invention provides a method of determining whether an animal possesses an antibody that specifically binds to a BVDV $E^{rns}$ protein, wherein said antibody specifically binds to an epitope present in a BVDV $E^{rns}$ protein, but which epitope is not present in a pronghorn pestivirus $E^{rns}$ protein.

DETAILED DESCRIPTION OF THE INVENTION

The following definitions may be applied to terms employed in the description of embodiments of the invention. The following definitions supersede any contradictory definitions contained in each individual reference incorporated herein by reference.

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular.

"About" or "approximately," when used in connection with a measurable numerical variable, refers to the indicated value of the variable and to all values of the variable that are within the experimental error of the indicated value (e.g., within the 95% confidence interval for the mean) or within 10 percent of the indicated value, whichever is greater.

The term "animal", as used herein, is meant to include any animal that is susceptible to BVDV infections, including but not limited to bovine, ovine, caprine, and porcine species, both domesticated and wild.

The term "antibody" or "antibodies", as used herein, refers to an immunoglobulin molecule able to bind to an antigen by means of recognition of an epitope. Immunoglobulins are serum proteins composed of "light" and "heavy" polypeptide chains having "constant" and "variable" regions and are divided into classes (e.g., IgA, IgD, IgE, IgG, and IgM) based on the composition of the constant regions. An antibody that is "specific" for a given antigen indicates that the variable regions of the antibody recognize and bind a specific antigen exclusively. Antibodies can be a polyclonal mixture or monoclonal. Antibodies can be intact immunoglobulins derived from natural sources or from recombinant sources, or can be immunoreactive portions of intact immunoglobulins. Antibodies can exist in a variety of forms including, for example, as, Fv, Fab', $F(ab')_2$, as well as in single chains. An antibody can be converted to an antigen-binding protein, which includes but is not limited to antibody fragments.

The term "antigen", as used herein, refers to a molecule that contains one or more epitopes (linear, conformational or both) that upon exposure to a subject will induce an immune response that is specific for that antigen. The term "antigen" can refer to attenuated, inactivated or modified live bacteria, viruses, fungi, parasites or other microbes. The term "antigen" as used herein can also refer to a subunit antigen, which is separate and discrete from a whole organism with which the antigen is associated in nature. The term "antigen" can also refer to antibodies, such as anti-idiotype antibodies or fragments thereof, and to synthetic peptide mimotopes that can mimic an antigen or antigenic determinant (epitope). The term "antigen" can also refer to an oligonucleotide or polynucleotide that expresses an antigen or antigenic determinant in vivo, such as in DNA immunization applications.

"Buffer" means a chemical system that prevents change in the concentration of another chemical substance, e.g., proton donor and acceptor systems serve as buffers preventing marked changes in hydrogen ion concentration (pH). A further example of a buffer is a solution containing a mixture of a weak acid and its salt (conjugate base) or a weak base and its salt (conjugate acid).

The terms "BVDV", "BVDV isolates" or "BVDV strains", as used herein, refer to bovine viral diarrhea viruses, including but not limited to type I and type II, that consist of the viral genome, associated proteins, and other chemical constituents (such as lipids). A number of type I and type II bovine viral diarrhea viruses are known to those skilled in the art and are available through, e.g., the American Type Culture Collection (ATCC®; Manassas, Va. 20108 USA). The bovine viral diarrhea virus has a genome in the form of RNA. RNA can be reverse transcribed into DNA for use in cloning. Thus, references made herein to nucleic acid and bovine viral diarrhea virus sequences encompass both viral RNA sequences and DNA sequences derived from the viral RNA sequences. The term "NADL" as used herein refers to a reference strain of BVDV, deposited in the ATCC as VR-534.

The term "cell line" or "host cell", as used herein, means a prokaryotic or eukaryotic cell in which a virus can replicate or be maintained.

"Cellular immune response" or "cell mediated immune response" is one mediated by T-lymphocytes or other white blood cells or both, and includes the production of cytokines, chemokines and similar molecules produced by activated T-cells, white blood cells, or both.

The term "chimeric" or "chimera", as used herein, means a microorganism, for example a virus, containing genetic or physical components derived from more than one progenitor.

The term "conventional BVDV vaccine", as used herein, means a vaccine based on a wild-type BVDV. The virus can be attenuated or inactivated. The virus is not genetically-modified, however.

The term "culture", as used herein, means a population of cells or microorganisms growing in the absence of other species or types.

The term "DIVA", as used herein, means to differentiate infected from vaccinated animals.

"Dose" refers to a vaccine or immunogenic composition given to a subject. A "first dose" or "priming vaccine" refers to the dose given on Day 0. A "second dose" or a "third dose" or an "annual dose" refers to an amount of such composition given subsequent to the first dose, which may or may not be the same vaccine or immunogenic composition as the first dose.

The term "epitope", as used herein, means the specific site of the antigen which binds to a T-cell receptor or specific antibody, and typically comprises from about 3 amino acid residues to about 20 amino acid residues, and can be continuous or discontinuous.

"Fragment" refers to a truncated portion of a protein or gene. "Functional fragment" and "biologically active fragment" refer to a fragment that retains the biological properties of the full length protein or gene. An "immunogenically active fragment" refers to a fragment that elicits an immune response.

The term "heterologous", as used herein, means derived from a different species or strain.

The term "homologous", as used herein, means derived from the same species or strain.

"Humoral immune response" refers to one that is at least in part mediated by antibodies.

"Immune response" in a subject refers to the development of a humoral immune response, a cellular immune response, or a humoral and a cellular immune response to an antigen. The immunogenic response may be sufficient for diagnostic purposes or other testing, or may be adequate to prevent signs or symptoms of disease, including adverse health effects or complications thereof, caused by infection with a disease agent.

"Immunogenic" or "Immunogenicity", as used herein, refers to the capability to elicit an immune response directed specifically against an antigen.

The term "immunogenic composition", as used herein, means a composition that capable of being recognized by the immune system, resulting in the generation of a specific immune response (i.e., has immunogenic activity) when administered alone or with a pharmaceutically acceptable carrier, to an animal.

The term "immunologically effective amount", as used herein, refers to the amount of an antigen effective to induce an immunogenic or immunological response in an animal. The immune response can comprise, without limitation, induction of cellular and/or humoral immunity.

"Isolated", as used herein, means removed from its naturally occurring environment. When referring to a microorganism, it can be either alone or in a heterologous host cell, or chromosome or vector (e.g., plasmid, phage, etc.). "Isolated bacteria," "isolated anaerobic bacteria," "isolated bacterial strain," "isolated virus" "isolated viral strain" and the like refer to a composition in which the bacteria or virus are substantial free of other microorganisms, e.g., in a culture, such as when separated from it naturally occurring environment. "Isolated," when used to describe any particularly defined substance, such as a polynucleotide or a polypeptide, refers to the substance that is separate from the original cellular environment in which the substance—such as a polypeptide or nucleic acid—is normally found. As used herein therefore, by way of example only, a recombinant cell line constructed with a polynucleotide of the invention makes use of the "isolated" nucleic acid. Alternatively, if a particular protein or a specific immunogenic fragment is claimed or used as a vaccine or other composition, it would be considered to be isolated because it had been identified, separated and to some extent purified as compared to how it may exist in nature. If the protein or a specific immunogenic fragment thereof is produced in a recombinant bacterium or eukaryote expression vector that produces the antigen, it is considered to exist as an isolated protein or nucleic acid. For example, a recombinant cell line constructed with a polynucleotide makes use of an "isolated" nucleic acid.

The term "multiplicity of infection" (M), as used herein, refers to a ratio of the number of microorganisms per cell, which details how much inoculum is going to be used in a given infection.

The terms "pathogen" or "pathogenic microorganism", as used herein, means a microorganism—for example a virus, bacterium, fungus, protozoan, or helminth—which is capable of inducing or causing a disease, illness, or abnormal state in its host animal.

The term "pestivirus", as used herein, means a RNA virus from the genus Pestivirus, of the family Flaviviridae. Pestiviruses include, but are not limited to, BVDV (type 1 and type 2), Classical Swine Fever Virus (CSFV), and Border Disease Virus (BDV), as well as pestiviruses isolated from species such as wild boar, buffalo, eland, bison, alpaca, pudu, bongo, various deer species, giraffe, reindeer, chamois and pronghorn antelope (Vilcek and Nettleton; *Vet Microbiol.* 116:1-12 (2006)).

"Pharmaceutically acceptable" refers to substances, which are within the scope of sound medical judgment, suitable for use in contact with the tissues of subjects without undue toxicity, irritation, allergic response, and the like, commensurate with a reasonable benefit-to-risk ratio and effective for their intended use.

The terms "prevent", "preventing" or "prevention", and the like, as used herein, mean to inhibit the replication of a microorganism, to inhibit transmission of a microorganism, or to inhibit a microorganism from establishing itself in its host. These terms and the like as used herein can also mean to inhibit or block one or more signs or symptoms of infection.

"Protection", "protecting", and the like, as used herein with respect to a vaccine or other composition, means that the vaccine or composition prevents or reduces the symptoms of the disease caused by the organism from which the antigen(s) used in the vaccine or composition is derived. The terms "protection" and "protecting" and the like, also mean that the vaccine or composition can be used to therapeutically treat the disease or one of more symptoms of the disease that already exists in a subject.

The terms “specific binding,” “specifically binds,” and the like, as used herein, are defined as two or more molecules that form a complex that is measurable under physiologic or assay conditions, and is selective. An antibody or other inhibitor is said to “specifically bind” to a protein if, under appropriately selected conditions, such binding is not substantially inhibited, while at the same time non-specific binding is inhibited. Specific binding is characterized by high affinity, and is selective for the compound or protein. Nonspecific binding usually has low affinity. Binding in IgG antibodies, for example, is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody carrying the antigen-binding domain will generally not bind other antigens.

The term “therapeutically effective amount”, as used herein, means an amount of a microorganism, or a subunit antigen, or polypeptides, or polynucleotide molecules, and combinations thereof, or a vaccine or a composition, needed to treat a disease in the subject to which it is administered.

The terms “treat”, “treating” or “treatment”, and the like, as used herein, mean to reduce or eliminate an infection by a microorganism. These terms and the like as used herein can also mean to reduce the replication of a microorganism, to reduce the transmission of a microorganism, or to reduce the ability of a microorganism to establish itself in its host. These terms and the like as used herein can also mean to reduce, ameliorate, or eliminate one or more signs or symptoms of infection by a microorganism, or accelerate the recovery from infection by a microorganism.

The terms “vaccinate” and “vaccinating” and the like, as used herein, mean to administer to an animal a vaccine or immunogenic composition.

The terms “vaccine” and “vaccine composition,” as used herein, mean a composition which prevents or reduces an infection, or which prevents or reduces one or more signs or symptoms of infection. The protective effects of a vaccine composition against a pathogen are normally achieved by inducing in the subject an immune response, either a cell-mediated or a humoral immune response or a combination of both. Generally speaking, abolished or reduced incidences of infection, amelioration of the signs or symptoms, or accelerated elimination of the microorganism from the infected subjects are indicative of the protective effects of a vaccine composition. The vaccine compositions of the present invention provide protective effects against infections caused by BVDV.

The term “veterinarily-acceptable carrier”, as used herein, refers to substances, which are within the scope of sound medical judgment, suitable for use in contact with the tissues of animals without undue toxicity, irritation, allergic response, and the like, commensurate with a reasonable benefit-to-risk ratio, and effective for their intended use.

The following description is provided to aid those skilled in the art in practicing the present invention. Even so, this description should not be construed to unduly limit the present invention as modifications and variations in the embodiments discussed herein can be made by those of ordinary skill in the art without departing from the spirit or scope of the present inventive discovery.

Detection, Diagnostic Methods, Kits

The present invention provides methods of determining whether an animal has had exposure to specific pestiviruses, either through infection or vaccination.

Vaccination which utilizes a DIVA vaccine—one which allows differentiation between infected and vaccinated animals—provides a means for assessing the exposure history of the animal subject. This differentiation can be accomplished via any of various diagnostic methods, including but not limited to an enzyme-linked immunosorbent assay (ELISA), which can be competitive, direct or indirect, lateral flow assay, Western blotting, PCR, radioimmunoassay, solid phase radioimmunoassay (SPRIA), electrochemiluminescent (ECL) assay, immunoblotting, immunoprecipitation, and immunostaining. These and other methods are readily recognized and known to one of ordinary skill in the art.

The chimeric pestiviruses described herein can be distinguished from wild-type BVDV strains in both their genomic composition and proteins expressed. Such distinction can allow for discrimination between vaccinated and infected animals. For example, a determination can be made as to whether an animal testing positive for BVDV in certain laboratory tests carries a wild-type BVDV strain or has been immunized with a conventional BVDV vaccine, or whether it has been administered a chimeric pestivirus or is uninfected.

A variety of assays can be employed for making the determination. For example, virus can be isolated from the animal testing positive for infection. Nucleic acid-based assays can include, but are not limited to, Southern or Northern blot analysis, PCR, and sequencing. Alternatively, protein-based assays can be employed. In protein-based assays, cells or tissues suspected of an infection can be isolated from the animal testing positive for BVDV. Cellular extracts can be made from such cells or tissues and can be subjected to, e.g., Western Blot, using appropriate antibodies against viral proteins that can distinctively identify the presence of either the chimeric pestivirus previously administered in a vaccine, or wild-type BVDV.

The extent and nature of the immune responses induced in the animal can be assessed by using a variety of techniques. For example, sera can be collected from the inoculated animals and tested for the presence or absence of antibodies specific for the chimeric virus.

In making such an assessment, it is critical that antibodies generated by the animal are specific for the test antigen in the assay, and not cross-reactive with the same antigen from other pestiviruses. It was not expected that antibodies which recognize and bind to the pronghorn pestivirus $E^{rns}$ protein would also bind to the $E^{rns}$ protein present on wild-type BVDV. However, repeated administrations of the chimeric pestivirus to cattle led occasionally to the generation of antibodies exhibiting limited cross-reactivity to the wild-type BVDV $E^{rns}$ protein. These cross-reactive antibodies are able to bind to the wild-type BVDV $E^{rns}$ protein bound to the plate (i.e. the test antigen), leading to results suggesting prior infection with wild-type BVDV or vaccination with a conventional BVDV vaccine—that is, a false positive result. Thus, a need exists to improve the accuracy and specificity of the assay. This can be accomplished by incubating the sera from animals in the presence of pronghorn $E^{rns}$ protein. The protein can be native—that is, purified from pronghorn pestivirus—or recombinantly-expressed. The addition of the pronghorn $E^{rns}$ protein can be done prior to addition of sera to the assay plate(s), or at the same time sera is added to the assay plate(s). This is effective in removing $E^{rns}$ cross-reactive antibodies, and results in a more accurate and reliable assay.

A kit of the present invention can comprise one or more reagents useful for the detection of and differentiation between (1) a BVDV-infected animal or one immunized with a conventional BVDV vaccine, and (2) an animal administered a chimeric pestivirus. The kit can include reagents for analyzing a sample for the presence of whole BVDV, or BVDV polypeptides, epitopes or polynucleotide sequences which are not present in the chimeric pestivirus. Alternatively, kits of the present invention can include reagents for analyzing a sample for the presence of a chimeric pestivirus, or polypeptides, epitopes or polynucleotide sequences which are not present in wild-type BVDV. The presence of virus, polypeptides, or polynucleotide sequences can be determined using antibodies, PCR, hybridization, and other detection methods known to those of skill in the art.

Another kit of the present invention can provide reagents for the detection of antibodies against particular epitopes. The epitopes are either present in the chimeric pestivirus and not present in wild type BVDV, or alternatively, are present in wild-type BVDV and not present in the chimeric pestivirus. Such reagents are useful for analyzing a sample for the presence of antibodies, and are readily known and available to one of ordinary skill in the art. The presence of antibodies can be determined using standard detection methods known to those of skill in the art.

In certain embodiments, the kits can include a set of printed instructions or a label indicating that the kit is useful for the detection and differentiation of BVDV-infected or BVDV-vaccinated animals from animals administered a chimeric pestivirus.

Antibody, Antibodies

Antibodies can either be monoclonal, polyclonal, or recombinant. The antibodies can be prepared against the immunogen or a portion thereof. For example, a synthetic peptide based on the amino acid sequence of the immunogen, or prepared recombinantly by cloning techniques or the natural gene product and/or portions thereof can be isolated and used as the immunogen. Immunogens can be used to produce antibodies by standard antibody production technology well known to those skilled in the art, such as described generally in Harlow and Lane, "Antibodies: A Laboratory Manual", Cold Spring Harbor Laboratory, Cold Spring Harbor, N.Y., (1988). Antibody fragments can also be prepared from the antibodies, and include Fab, F(ab')$_2$, and Fv, by methods known to those skilled in the art.

In the production of antibodies, screening for the desired antibody can be accomplished by standard methods in immunology known in the art. In general, both ELISAs and Western blotting are types of immunoassays that can be used, and both are well known to those skilled in the art. Both polyclonal and monoclonal antibodies can be used in the assays. The antibody used to bind BVDV $E^{rns}$ protein can be bound to a solid support substrate. Antibody can be conjugated with a detectable moiety or label. The detectable moieties contemplated for use in the present invention can include, but are not limited to, fluorescent, metallic, enzymatic, and radioactive markers including but not limited to biotin, gold, ferritin, alkaline phosphatase, b-galactosidase, peroxidase, urease, fluorescein, rhodamine, tritium, $^{14}C$, and iodination. The antibody conjugated with a detectable moiety can bind to BVDV $E^{rns}$ protein, as in a competitive ELISA assay, or it can bind to antibodies from an animal which bind to BVDV $E^{rns}$ protein, as in an indirect ELISA assay.

In conventional label conjugate specific binding assay techniques, a sample of the liquid medium to be assayed is combined with various reagent compositions. Such compositions include a label conjugate comprising a binding component incorporated with a label. The binding component in the conjugate participates with other constituents, if any, of the reagent composition and the ligand in the medium under assay to form a binding reaction system producing two species or forms of the conjugate, e.g., a bound-species (conjugate complex) and a free-species. In the bound-species, the binding component of the conjugate is bound by a corresponding binding partner whereas in the free species, the binding component is not so bound. The amount of analyte is proportional to the amount of bound versus unbound conjugate.

General Description of Assay Development

Cattle to which have been administered a chimeric pestivirus, in which the $E^{rns}$ protein of the BVDV is replaced with the $E^{rns}$ protein from a pronghorn pestivirus, can be distinguished from cattle naturally infected with a wild-type BVDV or immunized with a conventional BVDV vaccine through the use of the invention described herein. Cattle of various ages are either not treated or are administered three doses of either a live or inactivated chimeric pestivirus, or a live or inactivated BVDV, with about three weeks between each dose. Serum samples are collected 2-3 weeks or later following each administration, but prior to the next administration. To differentiate between cattle which received the chimeric pestivirus or those not receiving treatment, versus those infected by a field (wild-type) strain of BVDV or immunized with a conventional BVDV vaccine, serum samples are tested via a differential diagnostic assay.

For a competitive ELISA, wild-type BVDV or chimeric pestivirus $E^{rns}$ protein (naturally, synthetically or recombinantly derived) can be used as an antigen source in the assay. If $E^{rns}$ protein present on wild-type BVDV is used as the test antigen, a lack of binding by the labeled wild type BVDV $E^{rns}$-specific mAb indicates the presence of antibodies in the cattle serum that bind to the wild-type BVDV-specific epitope, indicative of a natural (wild-type) infection or immunization with a conventional BVDV vaccine. In contrast, serum from cattle given the chimeric pestivirus will not contain antibodies which bind to the wild-type BVDV $E^{rns}$ protein coating the plate. Therefore, the labeled wild type BVDV $E^{rns}$-specific mAb will bind to the bound protein, and result in subsequent color development.

In the above-described assay, it was surprising that antibodies which recognize and bind to the pronghorn pestivirus $E^{rns}$ protein would also bind to the $E^{rns}$ protein present on wild-type BVDV. Because repeated administration of the chimeric pestivirus to cattle occasionally resulted in the generation of antibodies that exhibited limited cross-reactivity to the wild-type BVDV $E^{rns}$ protein, which led to results suggesting prior infection with BVDV or vaccination with a conventional BVDV vaccine, a need existed to improve the accuracy and specificity of the assay.

For an improved competition ELISA, serum samples are incubated with recombinantly-expressed pronghorn pestivirus $E^{rns}$ protein either prior to or concurrently with the addition of cattle serum to the assay plates. This effectively removes antibodies which can bind to pronghorn pestivirus $E^{rns}$ protein, but have also developed cross-reactivity with wild-type BVDV $E^{rns}$ protein. Thus, color development in the assay indicates the animal is either naive to BVDV exposure or is vaccinated with the chimeric pestivirus, while no color development indicates that the animal was exposed to wild-type BVDV or vaccinated with a conventional BVDV vaccine.

The present invention is further illustrated by, but by no means limited to, the following example.

Example 1

A recombinant baculovirus expressing BVDV-NADL $E^{rns}$ was constructed. A DNA molecule encoding a genetic fusion of a 3' portion of the C gene of BVDV and the full length $E^{rns}$ gene was amplified by PCR from a plasmid containing full length of BVDV-NADL cDNA with primers Oligo 250 (SEQ ID NO: 1; 5'-CACCATGAAAATAGTGCCCAAAGAATC-3') and Oligo 252 (SEQ ID NO: 2; 5'-TTAAGCGTATGCTC-CAAACCACGTC-3'). The PCR product was cloned into pENTR™/D-TOPO (Invitrogen; Carlsbad, Calif.) and transformed into One Shot® Competent *E. coli* (Invitrogen) according to the manufacturer's instructions. The recombinant plasmid was extracted and the insert was confirmed by sequencing. This plasmid was designated pENTR-$E^{rns}$. pENTR-$E^{rns}$ and BaculoDirect™ Baculovirus Expression System (Invitrogen) were used to construct recombinant baculovirus expressing BVDV-NADL $E^{rns}$ protein according to the manufacturer's instructions. The recombinant baculovirus expressing BVDV-NADL $E^{rns}$ protein was generated, plaque purified, expanded, and stored at both 4° C. and −80° C. The expression of BVDV-NADL $E^{rns}$ protein in the recombinant baculovirus was confirmed by immunofluorescent staining and Western blot using BVDV $E^{rns}$ specific MAb 15C5 (Idexx Laboratories Inc.; Westbrook, Me.).

The pronghorn pestivirus $E^{rns}$ protein was expressed in baculovirus using a similar strategy. Expression of pronghorn $E^{rns}$ protein was confirmed by immunofluorescent staining and Western blot using anti-His (C-term) MAb (Invitrogen).

For production of the ELISA antigen, Sf21 or Sf9 cells in 100 ml suspension culture were infected with recombinant baculovirus stock at MOI's of 0.2 to 5. The cells were harvested after 2 to 4 days incubation at 27° C. The cells were centrifuged at low speed (about 800 g) for 10 min to collect the cells. The cells were lysed with native lysis/binding buffer (pH 8.0 50 mM NaH2PO4, 300 mM NaCl, 10 mM Imidazole, and 1% IGEPAL CA-630). The mixture was pipetted up and down to break up cell clumps, and then frozen at −80° C. for ≥1 hour. After thawing, the mixture was clarified by centrifuge at 8000 g for 20 minutes at 4° C. The final supernatant, designated Baculo-Pronghorn $E^{rns}$ lysate, was aliquoted and stored at −80° C.

In conducting the assay, the ELISA plates were coated overnight at 4° C. with 100 μl/well of MAb WB210 (Veterinary Laboratory Agency, Surrey, UK), which specifically binds to BVDV Type 1 $E^{rns}$ protein, diluted to 1 ug/ml in carbonate/bicarbonate buffer (pH 9.0). The next day, the plates were washed three times with PBST wash buffer (PBS containing 0.05% Tween 20) and incubated with blocking buffer (PBST plus 1% casein sodium salt) at 37° C. for 1 hour. The plates were subsequently washed three times with PBST, and 100 μl of Baculo-BVDV $E^{rns}$ lysate (diluted 1:1600 in PBS) was added to each well, and the plates were incubated at 37° C. for 1 hour. During this incubation period, 60 μl of a cattle serum sample was added to 60 μl sample diluent containing blocking buffer and a pre-determined concentration of Baculo-Pronghorn $E^{rns}$ lysate. The serum-diluent mixtures were incubated at room temperature for at least 30 minutes. Following three washes with PBST, serum-diluent mixtures were transferred to the wells of ELISA plates. Multiple wells were left blank on each plate, to serve as non-competing 15C5-HRP controls. Plates were incubated at 37° C. for 1 hour. Following three more washes with PBST, 100 μl MAb 15C5-HRP conjugate (specific to BVDV $E^{rns}$; diluted in blocking buffer) was added to each well at 37° C. for 1 hour. After three washes, 100 μl ABTS substrate (KPL, Gaithersburg, Md.) was added to each well, and incubated at room temperature for 20-60 minutes for color development. The optical density (OD) was measured at the wavelength of 405/490 nm. The percentage of OD inhibition from conjugate control for each serum sample is calculated by following formula:

% Inhibition=(OD of Sample)÷(Mean OD of 15C5-HRP Controls)×100%.

Six BVDV sero-negative cattle per treatment group were vaccinated with inactivated BVDV (NADL strain), the chimeric pestivirus, or no vaccine (NTX). Vaccinations were on three-week intervals. Serum samples were collected at each time point, prior to administering the vaccines. Samples were then tested in the above-described assay.

Results

The data presented in Table 1 represents a comparison of serologic responses of cattle administered experimental antigens and untreated controls. Data presented were generated using the original diagnostic assay and the improved diagnostic assay, which is the present invention. Serum samples were collected after administration to cattle of two doses of inactivated BVDV, or two doses of inactivated chimeric pestivirus. Based on several known BVDV positive and negative samples, the cutoff values for positive ("Pos"), negative ("Neg") or uncertain ("+/−") were defined as follows:

<40%=Pos

40%-50%=+/−

>50%=Neg

TABLE 1

| | | % Inhibition | |
|---|---|---|---|
| Animal ID | Treatment | Original Assay (undiluted) | Improved Assay (1:1) |
| 1358 | NTX | Neg | Neg |
| 1364 | NTX | Neg | Neg |
| 1365 | NTX | Neg | Neg |
| 1368 | NTX | Neg | Neg |
| 1372 | NTX | Neg | Neg |
| 1374 | NTX | Neg | Neg |
| 1351 | BVDV (NADL strain) | Pos | Neg |
| 1352 | BVDV (NADL strain) | Pos | Pos |
| 1354 | BVDV (NADL strain) | Pos | Neg |
| 1361 | BVDV (NADL strain) | Pos | Pos |
| 1363 | BVDV (NADL strain) | Pos | Pos |
| 1370 | BVDV (NADL strain) | Pos | Neg |
| 1355 | Chimeric pestivirus | NA | Neg |
| 1357 | Chimeric pestivirus | Neg | Neg |
| 1359 | Chimeric pestivirus | Neg | Neg |
| 1360 | Chimeric pestivirus | Neg | Neg |
| 1366 | Chimeric pestivirus | Neg | Neg |
| 1369 | Chimeric pestivirus | Pos | Neg |

The data presented in Table 2 represents a continuation of the experiment described above for Table 1. Here, serum samples were collected after administration of a third dose of either the inactivated BVDV or inactivated chimeric pestivirus.

TABLE 2

| | | % Inhibition | |
|---|---|---|---|
| Animal ID | Treatment | Original Assay (undiluted) | Improved Assay (1:1) |
| 1358 | NTX | Neg | Neg |
| 1364 | NTX | Neg | Neg |
| 1365 | NTX | Neg | Neg |
| 1368 | NTX | Neg | Neg |
| 1372 | NTX | Neg | Neg |
| 1374 | NTX | Neg | Neg |
| 1351 | BVDV (NADL strain) | Pos | Pos |
| 1352 | BVDV (NADL strain) | Pos | Pos |
| 1354 | BVDV (NADL strain) | Pos | Pos |
| 1361 | BVDV (NADL strain) | Pos | Pos |
| 1363 | BVDV (NADL strain) | Pos | Pos |
| 1370 | BVDV (NADL strain) | Pos | Pos |
| 1355 | Chimeric pestivirus | Pos | Neg |
| 1357 | Chimeric pestivirus | Pos | Neg |
| 1359 | Chimeric pestivirus | Pos | Neg |
| 1360 | Chimeric pestivirus | Neg | Neg |
| 1366 | Chimeric pestivirus | +/− | Neg |
| 1369 | Chimeric pestivirus | Pos | Neg |

The data presented in Table 3, generated using the original $E^{rns}$ DIVA assay and the improved $E^{rns}$ DIVA assay, represents a comparison of serologic responses in cattle administered three doses of either a live attenuated BVDV or a live chimeric pestivirus.

TABLE 3

| | | % Inhibition | |
|---|---|---|---|
| Animal ID | Treatment | Original Assay (undiluted) | Improved Assay (1:1) |
| 5688 | NTX | Neg | Neg |
| 5699 | NTX | Neg | Neg |
| 5700 | NTX | Neg | Neg |
| 5701 | NTX | Neg | Neg |
| 5706 | NTX | Neg | Neg |
| 5709 | NTX | Neg | Neg |
| 1351 | BVDV (NADL strain) | Pos | Neg |
| 1352 | BVDV (NADL strain) | Pos | Neg |
| 1354 | BVDV (NADL strain) | Pos | Neg |
| 1361 | BVDV (NADL strain) | Pos | Pos |
| 1363 | BVDV (NADL strain) | Pos | Pos |
| 1370 | BVDV (NADL strain) | Pos | Neg |
| 1355 | Chimeric pestivirus | Neg | Neg |
| 1357 | Chimeric pestivirus | Neg | Neg |
| 1359 | Chimeric pestivirus | Pos | Neg |
| 1360 | Chimeric pestivirus | Neg | Neg |
| 1366 | Chimeric pestivirus | Neg | Neg |
| 1369 | Chimeric pestivirus | Neg | Neg |

The data demonstrate that the additional step of incubating cattle serum with recombinantly-expressed pronghorn pestivirus $E^{rns}$ protein, prior to its addition to the assay plates, is effective in removing cross-reactive antibodies capable of binding to both BVDV and pronghorn $E^{rns}$ protein. Thus, the serological status of those animals receiving the chimeric pestivirus showed BVDV-negative in the improved DIVA assay, and not falsely BVDV-positive (i.e. infected with BVDV or vaccinated with a conventional BVDV vaccine).

Example 2

The DIVA assay described in Example 1 is combined in tandem with another BVDV-specific antigen capture assay or antibody assay, to determine if a negative sample detected with the DIVA assay of Example 1 (i.e., one that is from an animal either vaccinated with the chimeric pestivirus, or a naïve uninfected animal) is indeed naïve, or is instead from an animal vaccinated with the chimeric pestivirus.

The negative sample from the DIVA assay of Example 1 is tested for the presence of a second antigen or antibody to BVDV that will be present even in an animal that has been vaccinated with the chimeric pestivirus. In this assay, a sample from an animal that is determined "negative" for BVDV with the DIVA assay of Example 1 is further analyzed for the presence or absence of another BVDV-specific antigen or antibody. For example, the DIVA assay of Example 1 is combined with an antigen capture test or an antibody detection test for an antibody that specifically binds another BVDV antigen, e.g., BVDV E2 protein. Alternatively, the sample from an animal that is determined "negative" for BVDV with the DIVA assay of Example 1 is analyzed for antibodies specific for BVDV p80/125 (i.e. NS 2/3) non-structural protein. Assays for the detection of such proteins are commercially available and described, e.g., SERELISA® BVDV p80 Ab Mono Blocking kit (Synbiotics Corporation; Kansas City, Mo.)

An exemplary readout from a combination of the DIVA assay of Example 1 with an assay for an antibody that specifically binds another BVDV antigen, such as p80, will produce results as exemplified in Table 4.

TABLE 4

| | Readout by Indicated Assay | |
|---|---|---|
| Animal Status | DIVA | p80 |
| Naïve (uninfected; unvaccinated) | − | − |
| Infected with wild-type BVDV | + | + |
| Vaccinated with wild-type BVDV vaccine (live or killed) | + | + |
| Vaccinated with disclosed chimeric pestivirus vaccine (live or killed) | − | + |

Although the present invention has been described in considerable detail with reference to certain versions thereof, other versions are possible. Therefore, the scope of the appended claims should not be limited to the description of the versions contained herein.

What is claimed is:

1. A method of detecting the presence of an antibody that specifically binds to a bovine viral diarrhea virus (BVDV) $E^{rns}$ protein, said method comprising the steps of:

a) incubating a serum sample from an animal with pronghorn pestivirus $E^{rns}$ protein or a fragment thereof to which antibodies that cross-react with BVDV $E^{rns}$ bind, wherein said sample is incubated either prior to or concurrently with step b);

b) adding said sample from a) to an assay plate comprising bound BVDV $E^{rns}$ protein; and c) detecting in said sample the presence of said antibody, wherein the detecting comprises adding a labeled BVDV $E^{rns}$-specific monoclonal antibody to the assay plate, wherein the labeled antibody will bind to the bound BVDV $E^{rns}$ protein.

2. The method of claim 1, wherein said antibody to be detected specifically binds to at least one epitope present in a BVDV $E^{rns}$ protein, but not present in a pronghorn pestivirus $E^{rns}$ protein.

3. The method of claim 1, wherein the presence of said antibody indicates that the animal has either been infected with wild-type BVDV or immunized with a conventional BVDV vaccine.

4. The method of claim 1, wherein the absence of said antibody indicates that the animal has not been 1) infected with wild-type BVDV, or 2) immunized with a conventional BVDV vaccine, or has been immunized with a chimeric pestivirus expressing a pronghorn pestivirus $E^{rns}$ protein.

5. The method of claim 1, wherein the animal is an animal that is susceptible to BVDV infections.

6. The method of claim 5, wherein the animal is a bovine, ovine, caprine, or porcine species.

7. The method of claim 6, wherein the animal is a bovine.

8. A diagnostic kit useful for carrying out the method of claim 1, wherein said kit comprises components that facilitate the detection of the presence in the serum sample from an animal of an antibody to at least one BVDV $E^{rns}$ epitope not present in a pronghorn pestivirus $E^{rns}$ protein, wherein said components comprise pronghorn pestivirus $E^{rns}$ protein or a fragment thereof to which antibodies that cross-react with BVDV $E^{rns}$ bind, an assay plate comprising bound BVDV $E^{rns}$ protein, and a labeled BVDV $E^{rns}$-specific monoclonal antibody.

9. The diagnostic kit of claim 8, wherein said labeled BVDV $E^{rns}$-specific monoclonal antibody is an antibody that specifically binds to an epitope present in wild-type BVDV or a conventional BVDV vaccine, but which epitope is not present in a pronghorn pestivirus $E^{rns}$ protein.

10. The diagnostic kit of claim 8, wherein said kit comprises reagents for carrying out an assay selected from the group consisting of: an enzyme-linked immunosorbent assay (ELISA), a lateral flow assay, Western blotting, PCR, radioimmunoassay, solid phase radioimmunoassay, electrochemiluminescent assay, immunoblotting, immunoprecipitation, and immunostaining.

11. The method of claim 1, further comprising testing for the presence of (i) a BVDV protein that is not $E^{rns}$ or (ii) an antibody that specifically binds a BVDV protein that specifically binds a BVDV protein that is not $E^{rns}$.

12. The method of claim 11, wherein the sample is tested for the presence of an antibody that specifically binds to a BVDV protein, further wherein said protein is selected from the group consisting of p80 and E2.

* * * * *

SEQUENCE LISTING

```
<160> NUMBER OF SEQ ID NOS: 2

<210> SEQ ID NO 1
<211> LENGTH: 27
<212> TYPE: DNA
<213> ORGANISM: Artificial Sequence
<220> FEATURE:
<223> OTHER INFORMATION: primer Oligo 250

<400> SEQUENCE: 1
```

-continued

```
caccatgaaa atagtgccca aagaatc                                           27


<210> SEQ ID NO 2
<211> LENGTH: 25
<212> TYPE: DNA
<213> ORGANISM: Artificial Sequence
<220> FEATURE:
<223> OTHER INFORMATION: primer Oligo 252

<400> SEQUENCE: 2

ttaagcgtat gctccaaacc acgtc                                             25
```